US005500223A

United States Patent [19]

Behan et al.

[11] Patent Number: 5,500,223
[45] Date of Patent: Mar. 19, 1996

[54] ENCAPSULATING METHOD AND PRODUCTS CONTAINING ENCAPSULATED MATERIAL

[75] Inventors: John M. Behan, Ashford; Jeremy N. Ness, Canterbury; Keith D. Perring, Ashford, all of Great Britain

[73] Assignee: Unilever Patent Holdings B.V., Rotterdam, Netherlands

[21] Appl. No.: 170,989

[22] Filed: Dec. 21, 1993

Related U.S. Application Data

[60] Continuation of Ser. No. 962,907, Oct. 19, 1992, abandoned, which is a division of Ser. No. 766,780, Sep. 27, 1991, Pat. No. 5,185,155.

[30] Foreign Application Priority Data

Sep. 27, 1990 [GB] United Kingdom .................. 9021061

[51] Int. Cl.⁶ ............................................ A61K 9/48
[52] U.S. Cl. ...................... 424/451; 424/489; 424/490; 424/492
[58] Field of Search ................................ 424/451, 492, 424/490

[56] References Cited

U.S. PATENT DOCUMENTS

| 4,428,869 | 1/1984 | Munteanu et al. | 252/522 |
|---|---|---|---|
| 4,446,032 | 5/1984 | Munteanu et al. | 252/8.6 |
| 4,464,317 | 8/1984 | Thies | 264/4.3 |
| 4,482,606 | 11/1984 | Bousquet et al. | 428/402.2 |
| 4,579,779 | 4/1986 | Ohno | 424/490 |
| 4,931,284 | 6/1990 | Ekman et al. | 424/450 |
| 4,987,161 | 1/1991 | Yamamoto | 523/102 |
| 5,051,304 | 9/1991 | David et al. | 424/492 |
| 5,082,661 | 1/1992 | Melnik et al. | 424/451 |

FOREIGN PATENT DOCUMENTS

| 0227346 | 7/1987 | European Pat. Off. | C01B 33/18 |
|---|---|---|---|
| 0243166 | 10/1987 | European Pat. Off. | C01B 33/18 |
| 0246757 | 11/1987 | European Pat. Off. | C03C 17/25 |
| 0294206 | 12/1988 | European Pat. Off. | C01B 33/16 |
| 0309054 | 8/1989 | European Pat. Off. | C10M 173/00 |
| 0332259 | 9/1989 | European Pat. Off. | C11D 3/39 |
| 0332260 | 9/1989 | European Pat. Off. | C11D 3/50 |

OTHER PUBLICATIONS

Japanese Abstracts: No. 79–04743B and 75–82558W, Derwent Publications Ltd.

*Primary Examiner*—Thurman K. Page
*Assistant Examiner*—William E. Benston, Jr.
*Attorney, Agent, or Firm*—Cushman, Darby & Cushman

[57] ABSTRACT

An encapsulation process employs an aqueous dispersion of silica having a particle size not substantially greater than 100 nm. An emulsion is formed by high shear mixing of the silica dispersion with the material to be encapsulated and the emulsion is gelled. The process allows hydrophobic materials to be encapsulated in structures which have a high loading of the material and a good degree of imperviousness in the presence of other materials such as surfactants and mineral oils. Using the process, hydrophobic materials such as flavours, fragrances and cosmetic ingredients can be encapsulated for delayed release in a wide variety of products.

24 Claims, No Drawings

ENCAPSULATING METHOD AND PRODUCTS CONTAINING ENCAPSULATED MATERIAL

This is a continuation of application Ser. No. 07/962,907, filed on Oct. 19, 1992, which was abandoned upon the filing hereof which is a division of application Ser. No. 07/766,780, filed Sep. 27, 1991, now U.S. Pat. No. 5,185,155.

BACKGROUND OF THE INVENTION

This invention relates to a method of encapsulation, in particular of encapsulating hydrophobic liquids, and to encapsulated products containing such liquids. It is concerned particularly, although not necessarily exclusively, with encapsulated products that are to be used as additions, eg. for fragrance or flavour, to a base product.

There are many known micro-encapsulation methods which employ silica particles as an encapsulating material, the function of which is to allow a delayed but continuous release of the material encapsulated. In one type, exemplified by U.S. Pat. Nos. 4440542 and 4579779, the silica particles form an open-pored matrix which holds the material, especially liquids, in its interstices. In such a structure the outer pores are exposed and the encapsulated material may not be adequately shielded from premature release, whether by chemical reaction or by leaching. Furthermore, these porous structures rely on physical sorption of the encapsulated material and have a relatively limited liquid-silica ratio, or loading. That disadvantage is more pronounced if the encapsulated material is prone to premature release since this would be countered by increasing the density of the porous structure.

These porous structures can be produced in a modified form with a substantially impervious outer shell, as exemplified in U.S. Pat. No. 4464317. Although this prevents leaching of the encapsulated material it reduces still further the loading that can be achieved. A further disadvantage of the processes described in U.S. Pat. No. 4464317 is that they produce relatively large particles (eg. >500 µm), of a size that is unsuitable for many processes.

In another type of process described in EP294206A, porous spheroidal silica particles are formed which contain dispersed droplets of an encapsulated liquid. It is said that a loading can be achieved of up to 50% by weight of the silica, which is not a remarkable figure, yet the dry product still has considerable porosity since, when encapsulating a perfume, it is said that any wetting produces an appreciable increase of odour. Furthermore, the preparation of the product is complex and lengthy.

In another process described in EP309054A an aqueous emulsion is formed in which droplets of lubricating oil are coated with silica particles which stabilise the emulsion. The oil is added to a partially hydrophobed silica dispersion prepared from colloidal silica and the mixture is homogenised in a high-shear mixer. In the resulting emulsion the oil droplets are held as silica-coated droplets that are stable until ruptured by pressure, as when between bearing surfaces, to produce a lubricating film.

Experiments have shown, however, that if such emulsions are formed using hydrophobic materials, such as fragrances and flavours, that do not dissolve unaided in water, these emulsions cannot be usefully employed as additives to consumer products. This is because the emulsified material can make contact with and be dissolved by other components such as surfactants in cleaning or washing products or mineral oils in cosmetic products. The emulsified material will thus simply disperse when the silica-coated droplets are mixed into the product.

SUMMARY OF THE INVENTION

According to one aspect of the present invention, there is provided a process for encapsulating a hydrophobic material in which an aqueous dispersion of silica of particle size not substantially greater than 100 nm is produced, an emulsion is formed by high-shear mixing of said dispersion with the material to be encapsulated, and gelling said emulsion. Conveniently, the gelling is generally accomplished by the addition of a gelling agent, which may comprise an acidifying agent and/or a salt and/or a positively charged surfactant.

Observations indicate that the gelling step forms or stabilises a shell-like structure of silica particles around individual droplets of the hydrophobic material in the emulsion. The resulting capsules have sufficient stability to be used as such in certain applications. It is found, furthermore, that it is possible to give such shell-like structures significant strength and a good degree of imperviousness in relation to the encapsulated material.

The shell-like encapsulating structures formed are also found to be capable of holding relatively high loadings of hydrophobic material. According to another aspect of the invention, therefore, there is provided a micro-encapsulate comprising an outer silica layer and containing a hydrophobic material in which the loading of said material to the silica is at least 1.5:1 and is preferably greater than 2:1, eg. up to 100:1.

Typical products in which the micro-encapsulates can be incorporated include cosmetic products, such as skin cream and sunscreen formulations, detergent products such as laundry wash products, household cleaners, shampoos, hair conditioners and bleaches, and oral hygiene products such as toothpastes. Depending upon the product and its use, the encapsulation may be employed to protect materials against loss by evaporation during storage or hot processing, or against chemical degradation (particularly in products containing other, hostile ingredients), to improve the targeting of materials in use (eg. perfume deposition onto fabrics during washing and conditioning) particularly to assist triggered delivery through heat, shear or dissolution, or to extend activity (eg. of a fragrance or flavouring) through controlled delivery and evaporation.

Suitable and convenient silica materials include colloidal silica and fumed silica. Colloidal silica is supplied commercially as an alkaline solution (pH>9) and a hydrophobing agent may be added to help produce the aqueous dispersion. Suitable hydrophobing agents include positively charged surfactants such as cetyltrimethylammonium bromide (CTAB). Fumed silica forms an acidic emulsion (pH 3–5) which requires no hydrophobing agent.

By using silica particles having some hydrophobic character in the aqueous dispersion, or by giving them such a character by adding a hydrophobing agent, the particles tend to concentrate at the interface between the water and the hydrophobic material as high-shear mixing occurs and so coat the (dispersed) hydrophobic material. It is found possible, in fact, to obtain silica-stabilised emulsions having relatively high ratios of emulsified material to silica, with the weight of emulsified hydrophobic material at least equal to the weight of silica. At this stage, however, the silica particles are bound together too weakly to hold a hydrophobic material stably when incorporated in a product.

The porosity of the initial coating of silica particles is related to some extent to the silica particle size which may be up to 100 nm. By using silica with a relatively small particle size, preferably in the range 5–50 nm, or more advantageously 5–20 nm, a shell-like structure is obtained which can be strengthened and rendered substantially impervious after emulsification. Mixtures of silica particles of different sizes can also be used to improve packing and so improve further the stability of the shell-like structure.

The treatment after emulsification comprises a gelling step. It may be sufficient to perform that step using an appropriate gelling agent, but otherwise the gelling step can be followed with a further treatment.

In the first case, the gelling step can be carried out in a coacervation process using a positively charged compound such as a positively charged polymer or a gum or a silicone which, as it attaches itself to the silica shell, is able to form an outer layer on the capsule.

Alternatively gelling can be obtained by acidifying the emulsion to a pH value of approximately 8.0 to 5.0, preferably 6.5 to 5.5 by the addition of an acid or by changing the charge state of the silica shell by adding a surfactant or a salt such as $CaCl_2$. With this procedure, the product may be useful for limited applications, eg. as a slow-release air freshener or carpet freshener or deodorant. However, for most purposes further treatment may be needed to reduce the porosity of the silica shell and/or to otherwise modify the effective retention of the encapsulated product, eg. to increase the strength of the capsules against rupture.

There are a number of alternative treatments available for reducing the porosity of the capsules in the gelled product. The choice may depend on the form (eg. liquid or solid) of final product required. For example, by heating or adding a drying agent after gelling, a dried product can be obtained that is suitable for use in powder formulations, eg. to carry a fragrance in an air freshener or a laundry powder.

In another form of treatment, the capsules can be given an outer coating by blending the gelled material with a suitable material such as a liquid crystal forming surfactant or a polymer. Suitable surfactants may be selected from any of the major classes (ie. non-ionic, cationic, anionic and zwitterionic) and where appropriate their ability to form liquid crystal structures may be assisted by the inclusion of structuring aids such as steroids. Examples of suitable surfactants include Polyethoxylated fatty alcohols (eg. POE(2) cetyl alcohol) Sorbitan esters (eg. sorbitan monostearate) Glycerol esters (eg. glycerol monostearate) Phospholipids (eg. phosphatidylcholine) Fatty alcohols (eg. cetyl alcohol) Quaternaries (eg. dimethylditallowammonium chloride) Suitable polymers may include starch, modified starch, other polysaccharides (eg. gums), derivatised polysaccharides and synthetic polymers such as silicones, polyacrylics (eg. polyacrylamide) and polyvinyl pyrrolidones.

When treated with a liquid crystal forming surfactant, in particular, the capsules may be given a greater resistance to rupture, especially against abrasion, which can improve their efficacy for products such as toothpaste flavourings or sunscreen formulations. Addition of starch may be appropriate for a fragrance, eg. in a carpet freshener formulation when some of the fragrance will be held also by the starch as it precipitates out of solution while the product dries and will be released slowly after the carpet has dried. Preferably, with capsules such as these, having a further coating material, the encapsulated material forms at least 60% by weight of the encapsulate and may be present in up to 30 times the weight of the encapsulating material.

Micro-encapsulates prepared according to the invention can be incorporated in final products in any required proportion up to 99%, but for most purposes a minimum level of 0.1–0.2% is appropriate, in particular if the product also has a further amount of the hydrophobic material freely dispersed in it.

PREFERRED EMBODIMENTS OF THE INVENTION

The invention is illustrated by the following examples of some processes and products according to the invention. The first group of Examples 1–4 describe the formation of a preliminary emulsion with the silica particles.

EXAMPLE 1

0.01 g CTAB was dissolved in 75 g de-ionised water. 25 g colloidal silica (Ludox HS-40 from E I Du Pont de Nemours, mean particle size 12 nm) was then mixed with the water to form a homogeneous dispersion for encapsulating a perfume having the formulation: coumarin 0.5%, benzyl acetate extra 4.0%, benzyl salicylate 10.0%, dihydromyrcenol 10.0%, citronellol 10.0%, Lixetone (TM) 8.0%, methyldihydrojasmonate 5.0%, phenyl ethyl alcohol 10.0%, Traseolide (TM) 7.5%, Jasmopyrane (TM) forte 10.0%, linalol 10.0%, hexyl cinnamic aldehyde 8.0%, iso-longifolanone 3.0%, styrallyl acetate 1.0%, methylionone 3.0%. 75 g of the perfume was added to the dispersion while mixing in a high-shear mixer, eg. a Silverson mixer, for approximately 30 seconds. A milky-white emulsion resulted with a pH of approximately 9 in which droplets of the perfume were encapsulated by the silica. The capsule size was found to be in the range 2–5 μm and the weight ratio of silica to encapsulated material was 1:7.5.

EXAMPLE 2

Example 1 was repeated using 78 g de-ionised water, without CTAB, 2 g fumed silica (Aerosil 300 from Degussa AG, mean particle size 7 nm) with 20 g flavouring as the hydrophobic material. The formulation of the flavouring was: anethole 7.06% carvone laevo 8.90%, menthol laevo 10.0%, peppermint american 23.0%, spearmint american 51.0%, vanillin 0.04%. With the high-shear mixing a milky-white emulsion was produced with a pH of approximately 3.5. The particle size was in the range 2–30 μm and the weight ratio of silica to encapsulated material was 1:10.

EXAMPLE 3

An aqueous dispersion was prepared using 15 g Ludox HS-40 and 5 g Ludox SM, particle size 7 nm in 60 g de-ionised water. The dispersion was mixed in a high-shear mixer with 20 g parsol MCX (ex Givaudan) a sunscreen active, to give a milky-white emulsion with a pH of approximately 10. The particle size was in the ratio 5–10 μm and the weight ratio of silica to encapsulated material was 1:2.66.

EXAMPLE 4

Using the procedure of Example 1 a homogeneous dispersion was produced from 59.5 g de-ionised water and 0.5 g Aerosil 200, particle size 12 nm. This was mixed with 30 g of a perfume having the formulation: Galaxolide (TM) 7.5%, Lixetone (TM) 12.0%, lilial 7.0%, benzyl salicylate 7.2%, hexyl cinnamic aldehyde 13.0%, methyldihydrojasmonate 14.6%, phenyl ethyl alcohol 9.0%, dipropylene glycol 18.0%, litsea cubeba 5.0%, coumarin 0.06%, linalol 3.6%, hexyl salicylate 3.04%. A milky-white emulsion resulted with a pH of approximately 3.5. The particle size was 2–10 μm and the weight ratio of silica to encapsulated material was 1:60.

The emulsions obtained in these examples showed themselves to be unstable when added to a product base, the silica coatings being quite porous. As a consequence the encapsulated material eventually dispersed, eg. dissolving in an aqueous base. In the following group of Examples 5–9 the emulsion was acidified in a gelling operation giving a micro-porous silica shell structure. Porosity was reduced, giving products suitable for some end uses, as already mentioned, but generally further processing was desirable for completion of the encapsulation.

EXAMPLE 5

The pH of the emulsion of Example 1 was adjusted to 6.5 using 0.5M HCl (aqueous) and was allowed to stand for 72 hours. A thick cream was formed which "broke" on shaking to give a fluid emulsion.

EXAMPLE 6

The pH of the emulsion of Example 3 was adjusted to 6.0 using 0.5M HCl (aqueous) and the emulsion was allowed to stand for 48 hours. This produced a thick cream which "broke" on shaking to give a fluid emulsion. The pH was then increased to 7.5 to assist stability of the emulsion.

EXAMPLE 7

5 g of 0.1M $CaCl_2$ (aqueous) was added to 100 g of the emulsion of Example 1. Gelation took place over the course of several days.

EXAMPLE 8

10 g of 0.1M $CaCl_2$ (aqueous) was added to 100 g of the emulsion of Example 2. Rapid gelling followed to give a thick creamy product.

EXAMPLE 9

The pH of Example 4 was adjusted to 6.5 with 0.5M HCl (aqueous) and then 10 g of 5% w/w $CaCl_2$ in aqueous solution was added to 50 g of the emulsion. Rapid gelation followed.

The following group of Examples 10–15 illustrate final treatments for gelled intermediate products such as are produced by the preceding group of Examples 5–9 to reduce their porosity or otherwise to adapt them better to a particular end use.

EXAMPLE 10

A mixture of 4 g stearyl alcohol, 1.5 g sorbitan monostearate—Span 60 (ICI Speciality Chemicals)— and 0.25 g sodium lauryl sulphate were blended together by heating to form a homogeneous liquid. This mixture of the three surfactants was then added to 50 g of the gelated product of Example 7 which had been heated to the same temperature, while stirring gently. Stirring was continued while cooling. The product was a creamy stable emulsion suitable for incorporation into an aqueous detergent product.

EXAMPLE 11

5 g starch in the form of Capsul (National Starch) was dissolved in 40 g de-ionised water. The solution was dispersed in 50 g of the gelled product of Example 5. The resulting product was suitable for a carpet freshening product.

EXAMPLE 12

50 g of the gelled product of Example 5 was dehydrated with 50 g sodium tripolyphosphate to give a dry powder holding a fragrance that could be used in a laundry powder.

EXAMPLE 13

The gelled product of Example 5 was air-dried to give a dry powder containing 60% w/w perfume that could be used in a laundry powder.

EXAMPLE 14

50 g of the gelled product of Example 9 was prepared but with the flavouring described in Example 2 as the encapsulated material. This gelled product was further processed by the method of Example 10 using 4.5 g glycerol monostearate and 0.5 g CTAB. The final product was suitable for flavouring toothpaste.

EXAMPLE 15

The method of Example 14 was followed using 50 g of the gelled product of Example 6, 4.5 g arachidyl alcohol and 0.5 g CTAB, to produce an encapsulate carrying a sunscreen agent.

EXAMPLE 16

Following the method of Example 10, 50 g of the gelled product of Example 9 was mixed with 4.5 g POE(2) cetyl alcohol Brij 52 (ICI Speciality Chemicals) and 0.5 g sodium lauryl sulphate. The product was a stable emulsion suitable for perfuming a hard-surface cleaner.

The initial emulsions such as those in Examples 1–4 can alternatively be gelled in a complex coacervation process to reduce the porosity of the silica, even to the extent of rendering the shell substantially impervious, and to increase the strength of the encapsulation. This is illustrated in the following Examples 17–21.

EXAMPLE 17

The pH of the emulsion of Example 2 was adjusted to 7.5 using 1M HCl(aqueous). After standing for 6 hours, 1 g of gum acacia in a 10% aqueous solution was then added to 100 g of the emulsion. The product was suitable for inclusion in a dental care formulation.

EXAMPLE 18

The pH of the emulsion of Example 3 was adjusted to 7.0 using 0.5M HCl(aqueous). 2 g of quaternised starch derivative Celquat L-200 (National Starch Inc) in a 5% aqueous solution was added to 60 g of the emulsion. A thick creamy product resulted suitable for incorporation in a sunscreen preparation.

EXAMPLE 19

The pH of an emulsion prepared according to the method of Example 1 but using 37.5 g perfume was adjusted to 7.5 using 0.5M HCl(aqueous). 2 g of cationic silicone Abilquat 3270 (Th. Goldschmidt AG) was added to 75 g of the emulsion. The product was a stable emulsion suitable for inclusion in a hair conditioner.

EXAMPLE 20

To the product of Example 1 was added 5% w/w of Crystal 100 (Crosfield Chemicals Ltd), a sodium silicate formulation, while simultaneously adjusting the pH to and maintaining it at about 7.2% w/w of $CaCl_2$ in a 0.5M aqueous solution was added to gel the sodium silicate around the emulsion droplets. An improved encapsulate resulted.

EXAMPLE 21

To the product of Example 2 was added 5% w/w of Crystal 100 (Crosfield Chemicals Ltd), a sodium silicate formulation, while simultaneously adjusting the pH to and maintaining it at about 7.2% w/w of Celquat (National Starch Inc) in a 5% aqueous solution was added to gel the sodium silicate around the emulsion droplets. The product was suitable for flavouring an oral hygiene product.

Examples of the incorporation of the encapsulated materials of the preceding examples in aqueous base products will now be given.

EXAMPLE 22

A toothpaste was produced by first formulating three phases as follows, where the proportions are given as percentages by weight of the finished product:
(A) sorbitol (70% aq) 30.0%, sodium monofluorophosphate 0.85%, water 38.95%
(B) syloblanc 81 (silica) (W. R Grace & Co) 20.0%, sodium carboxymethylcellulose 1.60%, titanium dioxide 0.50%
(C) sorbitol (70% aq) 5.0%, NaOH (50% aq) 0.40%, empicol LXV (Albright and Wilson) 1.50%, saccharin 0.20%. Phases A and B were mixed thoroughly under high-shear for 30 minutes. Phase C was then stirred in under vacuum while maintaining the temperature at 40° C. Finally 1% flavour in the form of an encapsulated product containing a flavouring was mixed in under low shear for 15 minutes.

To test the comparative efficacy of the encapsulate stabilising measures employed in accordance with the invention three toothpaste samples were prepared each with the products of one of Examples 2, 8 and 14 added to the base, and a fourth sample was prepared with flavouring agent treated in accordance with Example 14 but without previously producing an emulsion of the agent with silica particles. A panel of trained evaluators assessed the products and reported a substantially greater flavour impact with the sample containing the silica-encapsulated product of Example 14 indicating that in comparison with all of the other samples the capsules had retained substantially more of the flavouring to release it upon use.

EXAMPLE 23

A skin cream was produced, first formulating two phases
(A) Emulgin B1 (Henkel Chemicals Ltd) 3.0%, Eutanol G (Henkel Chemicals Ltd) 22.0%, iso-propyl myristate 5.0%, glycerol monostearate 15.0%
(B) Hygroplex HHG (Henkel Chemicals Ltd) 3.0%, preservative q.s, purified water 51.8%. Each phase was heated separately to 70° C. Phase B was then mixed into phase A with constant stirring which continued until the resulting cream was cool. To this was then added 1% of an encapsulation product containing a perfume.

The skin cream base was used for four test samples containing perfume encapsulated by the processes of Examples 1, 7, 10 and 20 respectively. Examination by microscope showed that the samples using the encapsulates of Examples 1 and 7 were unstable, the capsules simply dispersing in the first and the perfume leaching out in the second, whereas the products of Examples 10 and 20 were stable in the product.

It will be understood that these and other products incorporating micro-encapsulates prepared in accordance with the invention may include free further hydrophobic compounds as fragrances, flavourings etc.

We claim:

1. A micro-encapsulate comprising an outer silica layer encapsulating a water-insoluble hydrophobic material selected from the group consisting of flavors, fragrances and sunscreen actives, said encapsulate being obtained by a process which comprises providing an aqueous dispersion of silica wherein the silica is in the form of particles substantially all of which have a particle size not greater than 100 nm;

forming an emulsion of said dispersion and said hydrophobic material to be encapsulated by mixing said dispersion and said hydrophobic material under high shear conditions; and gelling said emulsion containing the hydrophobic material whereby stable silica capsules comprising silica particles around droplets of the hydrophobic material are formed.

2. A micro-encapsulate according to claim 1 wherein the silica are in the form of colloidal silica or fumed silica having a size not substantially greater than 50 nm.

3. A micro-encapsulate according to claim 1 wherein the weight of encapsulated material to silica is at least 1.5:1.

4. A micro-encapsulate according to claim 1 wherein the gelling tap comprises at least one of the steps of (i) acidifying the emulsion (ii) adding a salt and (iii) adding a positively charged surfactant.

5. A micro-encapsulate according to claim 1 wherein a material is coated onto the capsules to reduce their porosity.

6. A micro-encapsulate according to claim 1 wherein the emulsion is galled by the addition of a positively charged material that forms an outer coating on the capsules.

7. A detergent product comprising at least 0.02% by weight of a micro-encapsulate prepared according to the process of claim 1 wherein the hydrophobic material is a perfume.

8. A detergent product comprising at least 0.02% by weight of a micro-encapsulate prepared according to the process of claim 1 where the hydrophobic material is a perfume, said detergent product given a formulation for use as one of the products of the consisting of a laundry wash product, a household cleaner, a bleach, a shampoo and a hair conditioner.

9. An oral hygiene product comprising at least 0.01% by weight a micro-encapsulate prepared according to the method of claim 1 wherein the hydrophobic material provides an action component of the product selected from at least one of the group consisting of a flavor, a food ingredient and a therapeutic agent.

10. A micro-encapsulate according to claim 1 wherein the silica capsules have a mean particle size smaller than 500 µm.

11. A composition of matter comprising:
(i) the micro-encapsulate of claim 1 mixed with
(ii) a plurality of further materials at least some of which are present as a liquid.

12. A micro-encapsulate according to claim 3 wherein the weight ratio of encapsulated material to silica is greater than 2:1.

13. A micro-encapsulate according to claim 4 wherein a material selected from the group consisting of a liquid-crystal-forming surfactant, a starch, and a polymer is coated onto the capsules to reduce their porosity.

14. A micro-encapsulate according to claim 6 wherein said material is selected from the group consisting of a positively charged polymer, a gum and a silicone.

15. A micro-encapsulate according to claim 5 wherein the encapsulated material forms at least 60% of the weight of the capsules.

16. A composition of matter according to claim 11 wherein said further materials comprise at least one material selected from the group consisting of surfactants and hydrophobic oils.

17. A composition of matter according to claim 11 wherein said further materials comprise water together with at least one material selected from the group consisting of surfactants and hydrophobic oils.

18. A composition of matter according to claim 17 which is selected from the group consisting of a skin cream, a laundry washing detergent powder, a household cleaner, a bleaching product, a shampoo and a hair conditioner.

19. A micro-encapsulate comprising an outer silica layer encapsulating a water-insoluble hydrophobic material selected from the group consisting of flavors, fragrances and sunscreen actives, in which the silica layer consists of silica particles of size not greater than 100 nm, and the loading of the hydrophobic material to the silica is at least 1.5:1.

20. A micro-encapsulate according to claim 19 wherein the silica capsules have a mean particle size smaller than 500 µm.

21. A composition of matter comprising:
(i) the micro-encapsulate of claim 19 mixed with
(ii) a plurality of further materials at least some of which are present as a liquid.

22. A composition of matter according to claim 21 wherein said materials comprise at least one material selected from the group consisting of surfactants and hydrophobic oils.

23. A composition of matter according to claim 21 wherein said further materials comprise water together with at least one material selected from the group consisting of surfactants and hydrophobic oils.

24. A composition of matter according to claim 23 which is selected from the group consisting of a skin cream, a laundry washing detergent powder, a household cleaner, a bleaching product, a shampoo and a hair conditioner.

* * * * *